(12) United States Patent
Kraszewski et al.

(10) Patent No.: US 9,206,209 B2
(45) Date of Patent: Dec. 8, 2015

(54) NUCLEOTIDE ANALOGUE, METHOD OF SYNTHESIS OF NUCLEOTIDE ANALOGUE, USE OF NUCLEOTIDE ANALOGUE, ANTIVIRAL PRO-NUCLEOTIDE, PHARMACEUTICAL COMPOSITION

(75) Inventors: Adam Kraszewski, Poznan (PL); Joanna Romanowska, Lubon (PL); Michal Sobkowski, Poznan (PL); Agnieszka Szymanska-Michalak, Sroda Wlkp (PL); Jacek Stawinski, Poznan (PL); Jerzy Boryski, Poznan (PL); Andrzej Lipniacki, Warsaw (PL); Andrzej Piasek, Warsaw (PL)

(73) Assignees: INSTYTUT CHEMII BIOORGANICZNEJ PAN, Poznan (PL); NARODOWY INSTYTUT LEKOW, Warsaw (PL)

( * ) Notice: Subject to any disclaimer, the term of this patent is extended or adjusted under 35 U.S.C. 154(b) by 208 days.

(21) Appl. No.: 13/879,709

(22) PCT Filed: Oct. 13, 2011

(86) PCT No.: PCT/PL2011/000103
§ 371 (c)(1),
(2), (4) Date: Jul. 16, 2013

(87) PCT Pub. No.: WO2012/053917
PCT Pub. Date: Apr. 26, 2012

(65) Prior Publication Data
US 2013/0316970 A1    Nov. 28, 2013

(30) Foreign Application Priority Data

Oct. 19, 2010  (PL) .......................... 392702

(51) Int. Cl.
| *A01N 43/04* | (2006.01) |
| *A61K 31/70* | (2006.01) |
| *C07H 19/04* | (2006.01) |
| *C07H 19/048* | (2006.01) |
| *C07H 19/10* | (2006.01) |
| *C07H 19/20* | (2006.01) |
| *C07F 9/02* | (2006.01) |
| *C07F 9/6561* | (2006.01) |
| *C07F 9/6558* | (2006.01) |

(52) U.S. Cl.
CPC ......... *C07F 9/65616* (2013.01); *C07F 9/65586* (2013.01); *C07H 19/10* (2013.01); *C07H 19/20* (2013.01)

(58) Field of Classification Search
CPC . C07F 9/65616; C07F 9/65586; C07H 19/10; C07H 19/20
See application file for complete search history.

(56) References Cited

U.S. PATENT DOCUMENTS

| 6,638,919 B2 * | 10/2003 | McGuigan et al. ............. 514/81 |
| 7,608,599 B2 * | 10/2009 | Klumpp et al. ................. 514/43 |
| 2001/0031745 A1 | 10/2001 | McGuigan et al. |
| 2007/0042988 A1 | 2/2007 | Klumpp et al. |
| 2008/0249066 A1 | 10/2008 | Quart et al. |

FOREIGN PATENT DOCUMENTS

| CN | 1290707 A | 4/2001 |
| WO | 2004113360 A1 | 12/2004 |
| WO | 2008087558 A2 | 7/2008 |

OTHER PUBLICATIONS

Romanowska, et al., "Aryl nucleoside H-phosphonates. Part 16: Synthesis and anti-HIV-1 activity of di-aryl nucleoside phosphotriesters", Bioorganic & Medicinal Chemistry, Feb. 23, 2009, pp. 3489-3498, vol. 17; Nr: 9, Pergamon, GB.
Jochum, et al., "Biolabile constructs for pronucleotide design", Journal of Organometallic Chemistry, Dec. 15, 2004, pp. 2614-2625, vol. 690, Nr: 10, Elsevier-Sequoia S.A., Lausanne, CH.
Egron, et al., "S-Acyl-2-thioethyl Phosphoramidate Diester Derivatives as Mononucleotide Prodrugs", Journal of Medicinal Chemistry, Sep. 13, 2003, pp. 4564-4571, vol. 46, Nr: 21, American Chemical Society, US.
Romanowska, et al., "Aryl H-Phosphonates 17: ( N-Aryl)phosphoramidates of Pyrimidine Nucleoside Analogues and Their Synthesis, Selected Properties, and Anti-HIV Activity", Journal of Medicinal Chemistry, Aug. 11, 2011, pp. 6482-6491, vol. 54, Nr: 19, American Chemical Society.

* cited by examiner

Primary Examiner — Lawrence E Crane
(74) Attorney, Agent, or Firm — Walker & Jocke

(57) ABSTRACT

An exemplary emboidment is related to a pharmaceutical composition of the class of nucleotide analogues and antiviral pro-nucleotides useful in partial or complete inhibition of human immunodeficiency virus (HIV). An exemplary embodiment is expressed in the formula (XVI):

(XVI)

where X stands for $N_3$ and B stands for thymidine-1-yl, or X stands for H and B stands for uracil-1-yl or adenin-1-yl or hypoxanthin-1-yl. A method of synthesis of the nucleotide analogue using a phosphorylating agent for synthesis of the nucleotide analogue is provided.

17 Claims, No Drawings

NUCLEOTIDE ANALOGUE, METHOD OF SYNTHESIS OF NUCLEOTIDE ANALOGUE, USE OF NUCLEOTIDE ANALOGUE, ANTIVIRAL PRO-NUCLEOTIDE, PHARMACEUTICAL COMPOSITION

CROSS-REFERENCES TO RELATED APPLICATIONS

This application is a national stage entry of PCT/PL2011/000103, which claims the benefit of foreign priority document P 392 702 filed on 19 Oct. 2010.

BACKGROUND

The subject matter of the invention are nucleotide analogues, antiviral pro-nucleotides, a use of nucleotide analogues and pharmaceutical composition, a phosphorylating agent for synthesis of nucleotide analogue, and a method of synthesis of nucleotide analogue. More precisely, the invention applies to the new group of nucleotide analogues and their use in partial or complete inhibition of human immunodeficiency virus (HIV).

There were described many masked nucleotide derivatives called pro-nucleotides, which were converted in the living cells into biologically active nucleotides. Among pro-nucleotides investigated for combating viruses, including HIV, the best results which made these compounds good candidates for therapeutic applications, were obtained for the nucleotide derivatives (covered with patents) called pro-nucleotides, in which nucleosides were 3'-azido-3'-deoxythymidine (AZT), 2',3'-dideoxyuridine (ddU), 2',3'-dideoxyadenosine (ddA), 2',3'-dideoxyinosine (ddI), 2',3'-dideoxy-2',3'-didehydrothymidine (d4T), 9-[9(1,3-dihydroxy-2-propoxy)methyl]guanine, acyclovir (ACV), 2',3'-dideoxycytidine (ddC), 2',3'-dideoxy-3'-thiacytidine (3TC).

Bis-pivaloyloxymethyl nucleoside phosphotriesters depicted with formula (I),

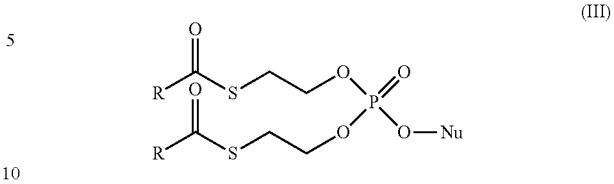

are called pivaloyloxymethyl (POM) pro-nucleotides [Sastry J. K. et al., *Mol. Pharmacol.*, 1992, 41, 441-445]. Nucleoside bis-pivaloyloxymethyl [R=C(CH$_3$)$_3$] (POM) phosphotriesters are pro-nucleotides which are converted into respective nucleoside phosphates by means of enzymatic hydrolysis of carboxylic ester of the side chain of pro-nucleotide phosphate masking group. Generated in this way hydroxymethylene functionality, rearranged spontaneously and produced unprotected nucleoside phosphate depicted with formula (II) and formaldehyde.

Nucleoside phosphotriesters depicted with formula (III)

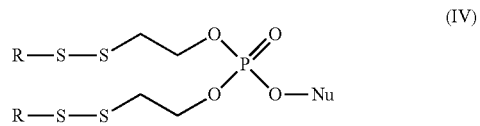

represents bis(S-acylthioethyl) (SATE) pro-nucleotides [Johum A., et al., *Organomet. Chem.*, 2005, 690, 2614-2625]. Compound of type (III) represents a whole family of anti-HIV bis-SATE nucleoside phosphotriesters (bis-SATE pro-nucleotides). Conversion of these compounds into unprotected phosphates of type (II) is initiated with enzymes—carboxyesterases, which hydrolyse carboxylic esters of S-acylthioethyl group and generates 2-thioethyl functionality that spontaneously undergoes elimination with formation of nucleosid-5'-yl phosphate of type (II). SATE nucleotides of type (III) are undoubtedly pro-nucleotides, due to they are internalized into cells as such and in the way described above generated awaited unmasked nucleotides of type (II). An anti-HIV potency of bis-SATE phosphotriesters of type (III) was described for derivatives of many nucleoside analogues of known anti-HIV activity. Unfortunately, bis-SATE pro-nucleotides (III) although disclosed advantageous pharmacokinetic parameters, bear some inconveniences because they are poorly soluble in water and also because the intermediate phosphodiester appeared to be rather poor substrate for enzymes hydrolyzing carboxylic esters due to close vicinity of phosphate anion (after removing of the first SATE group). There are known SATE derivatives which partially by-passed above inconveniences. There are known combinations of the phosphotriester SATE group with other different type of phosphate masking group of pro-nucleotides e. g. phenyl or phosphoramidate type ones.

The next group are bis(dithioethyl)nucleoside phosphotriesters—dithioethyl pro-nucleotides (DTE) [Gosselin G. et al., *Acta Biochem. Polon.*, 1996, 43(1), 195-208] having the formula (IV)

The DTE groups mask the phosphate moieties in pro-nucleotides (IV), and are removed analogously as the SATE but with an aid of reductase enzymes that cleave disulfide bonds yielding a 2-thioethyl phosphodiester group, which undergoes subsequently an intramolecular elimination, unmasking the phosphate moiety. This type of pro-nucleotides does not exhibit any particular antiviral activity in comparison to the others.

Cyclosaligenyl nucleoside phosphotriesters—cyclo-Sal pro-nucleotides [Meier, C., Balzarini, J., *Antiviral Res.*, 2006, 71, 282-292] have the formula (V)

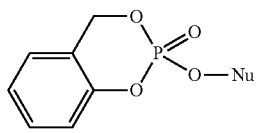

(V)

Cyclo-Sal pro-nucleotides under in vitro cell culture conditions and, presumably, under in vivo physiological conditions as well, form nucleoside phosphates of type (II) by way of chemical hydrolysis exclusively. Hydrolysis of cyclic phosphotriester of a formula (V) is regiospecific towards an aryl phosphoester bond cleavage. The generated benzyl phosphoester is transformed into the final nucleoside 5'-phosphate of type (II), also by way of chemical hydrolysis. The investigated cyclo-Sal pro-nucleotides were directed towards HIV inhibition (AZT, ddA, d4G, d4T derivatives) and also towards hampering of HSV propagation (ACV derivatives). In the case of HIV inhibition the best results were observed for a d4T cyclo-Sal derivative.

Diaryl nucleoside phosphotriesters having the formula (VI)

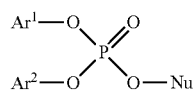

(VI)

are diaryl pro-nucleotides [Kraszewski A., et al., *Bioorg. Med. Chem.*, 2009, 17, 3489-3498]. The concept of action of pro-nucleotides of type (VI) is based on a selection of the aryl phosphoester groups securing their appropriate susceptibility to chemical hydrolysis under physiological conditions. The aryl nucleoside phosphodiesters formed are good substrates for phosphoesterases, which hydrolyze them to the desired nucleoside 5'-phosphates of type (II). With a proper choice of phosphoester aryl groups the diaryl phosphotriesters of type (VI) are pro-nucleotides with a high anti-HIV activity.

Phosphoramidate diesters have the formulas (VII) and (VIII) [Cahard D., *Mini-Rev. Med. Chem.*, 2004, 4, 371-381]

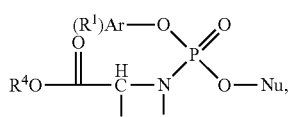

(VII)

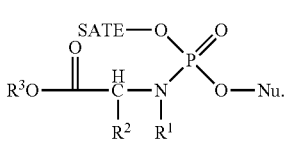

(VIII)

Phosphoramidate diesters of type (VII) and (VIII), amino acid derivatives, are structurally distinctive pro-nucleotides with the amide group formed by an amino acid bound to the phosphorus atom through the nitrogen atom of the α-amino group. Thus, it is an unequivocally defined group of pro-nucleotides. It is proven that phosphoramidate diesters of type (VII) and (VIII) act as pro-nucleotides. Anti-HIV activity of these compounds is tightly correlated with the kind of nucleoside (Nu), the structure and the kind of amino acid residue ($R^1$, $R^2$, and $R^3$) and the aryl moiety (Ar). For example, for AZT derivative of type (VII) the best results were obtained for Ar=phenyl and tryptophan as the amino acid moiety, for which the antiviral activity was similar to that of AZT, while the cytotoxicity was significantly lower.

The pro-nucleotides of type (IX) are derivatives of other amines [Jochum A., et al., *J. Organometal Chem.*, 2005, 690, 2614-2625]

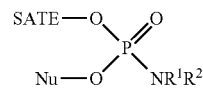

(IX)

It was proved that antiviral pro-nucleotides do not have to be amino acid derivatives. The investigated derivatives of simple amines exhibited the same or better pharmacokinetic parameters than those of analogous amino acid derivatives. It is assumed that in the compounds of type (IX) the SATE group is eliminated as the first one yielding phosphoramidate monoester that in turn is converted into nucleoside 5'-phosphate of type (II) in enzyme-catalyzed reactions. The compounds of type (IX) act as pro-nucleotides and show the anti-HIV activity higher or comparable to their parent nucleosides, while their toxicity is significantly lower.

Nucleoside bis(phosphoramidates) are pro-nucleotides having the formula (X) [Shipitsyn A. V., *Nucleos. Nucleot. & Nucleic Acids*, 2003, 22(5-8), 963-966]

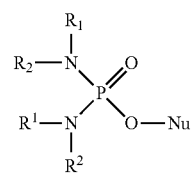

(X)

The anti-HIV activity of nucleoside bis(phosphoramidates) of type (X) was investigated. The activity and cytotoxicity of these compounds was correlated tightly with the kind of nucleoside residue (AZT and d4T) and the substituents of the nitrogen atoms of the phosphordiamidate residues. Nucleoside 5'-phosphate of type (II) is formed from the compounds of type (X) in a stepwise chemical or enzyme-aided hydrolysis, the mechanism of which is likely, however still assumed only.

Nucleoside phosphoramidates are pro-nucleotides having the formula (XI) [Wagner C. R., et al., *Mini-Rev. Med. Chem.*, 2004, 4, 409-419]

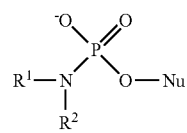

(XI)

All pro-nucleotides of type (XI) described so far are nucleoside phosphoramidate derivatives of amino acids. It was proven that these compounds enter the cells as such and are subsequently transformed into the respective nucleoside 5'-phosphate of type (II) with the aid of phosphoamidase enzymes present in the cells. A number of pro-nucleotides of type (XI) are described, namely the derivatives of several nucleoside analogues of known antiviral (AZT, d4T, ddC, 3TC, ddA) and anticancer (5-fluoro-2'-deoxyuridine) activity. They display high antiviral activity and low toxicity. These parameters point to the compounds of type (XI) as important potential antiviral and anticancer therapeutics.

The only commercially available nucleotide drug used in AIDS therapy is the tenofovir having the formula (XII)

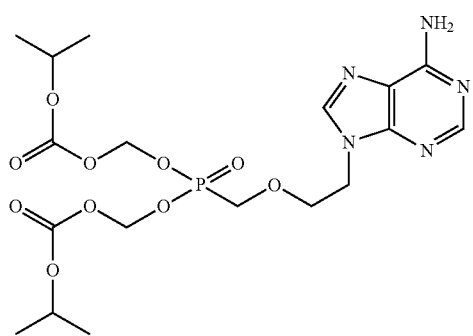

(XII)

It is a substituted C-phosphonate of an acyclic purine nucleoside, the assumed mode of action of which classifies it as a drug of the pro-nucleotide type. Its structure resembles the POM compounds (the type (I) pro-nucleotides) and most likely it acts in the same manner, i.e. the decomposition of carbonate ester in the side chain releases the phosphonate residue and facilitates its further conversion into triphosphate, which is able to inhibit HIV replication.

In US 2001031745 patent (published on 2001, Oct., 18) a number of chemical compounds comprising nucleoside phosphoramidates, their preparation and therapeutic use in treating viral infections, particularly HIV and HBV, were disclosed. These compounds contain a substituted adenine analogue moiety—2-amino-6-(cyclopropylamino)-9H-purin-9-yl. The compounds display antiviral activity and are stable in acid environment. The application comprises also salts and esters of the phosphoramidates. A representative compound of the application is (1S, 4R)-4-[2-amino-6-(cyclopropylamino)-9H-purin-9-yl]-2-cyclopentene-1-methylphenyl(methoxy-L-alaninyl)phosphoramidate.

In CN 1290707 patent (published on 2001, Apr., 11) a nucleoside 5'-thiophosphoryl amino acid ester compound, its preparation and application was disclosed. The compound was prepared through the processes of dissolving thiophosphoryl trichloride in dried tetrahydrofuran, addition of carbamate hydrochloride through stirring, dripping acid binding agent to react, filtering, rotating distillation to eliminate solvent and other low boiling point matters, hydrolysis in ammonia water and final silica gel chromatography. The compound of the invention exhibited antiviral, antitumor and HIV resisting activity and may have medical applications.

The US 2007042988 patent (published on 2007, Feb., 22) novel nucleotide compounds were disclosed, being phosphoramidate mono- and diesters prepared from modified nucleotides bonded with variously substituted amino acids and their analogues. The compounds were useful for the treatment of Hepatitis C Virus (HCV) mediated diseases. The invention further provided methods for treatment or prophylaxis of HCV mediated diseases with disclosed compounds and pharmaceutical compositions comprising these compounds.

In WO 2004113360 patent (published on 2004, Dec., 29) novel biologically active derivatives of 3'-azido-3'-deoxythymidine and 2',3'-dideoxy-2',3'-didehydrothymidine 5'-phosphates were disclosed as well as their application as antiviral agents, primarily against HIV. The invention makes it possible to develop and use novel compounds which are resistant to the action of phosphatases, capable to penetrate inside a cell and exhibit selective activity for suppressing cDNA biosynthesis which is catalyzed by the HIV reverse transcriptase. The disclosed compounds, i.e. phosphoramidates of nucleoside analogues comprising 5'-dimorpholinephosphordiamidate of 2',3'-dideoxy-2',3'-didehydrothymidine and 5'-dimorpholinephosphordiamidate of 3'-azido-3'-deoxythymidine, inhibit HIV replication and have defined formulas.

In US 2008249066 patent (published on 2008, Oct., 9) compounds useful in the treatment of viral diseases, compositions comprising them and methods of using them, are described. The compounds of the invention comprise a nucleoside or nucleoside analog linked usually through a phosphate group to one of selected groups of a lipid residue. The compounds described in the patent can be used for treating HIV infection, AIDS and other viral infections.

In WO 2008087558 patent (published on 2008, Jul., 24) compounds useful as antiviral or antitumor agents are presented. The compounds comprise nucleotide analogues that comprise tetrahydrofuranyl or tetrahydrothienyl moieties with quaternary centres at the 3' position. The nucleotide analogues can be used to inhibit cancer or viruses. The invention also describes pharmaceutical formulations comprising the compounds designed to treat, prevent, or inhibit the diseases or conditions associated with cancers and viruses.

Despite numerous known solutions exploiting nucleoside derivatives as compounds for treating viral diseases, there is still a continuous need for an efficient solution allowing preparation of pharmaceutical compositions comprising water-soluble compounds showing the same or higher activity as the starting nucleoside and displaying simultaneously low toxicity.

The aim of the current invention is to find efficient compounds being a novel group of nucleotide derivatives, the physicochemical properties and anti-HIV pharmacokinetic parameters of which would be better than those of the parent nucleoside analogues. The invention applies to compounds that would be pro-nucleotides without chiral centres that could affect the transformation of the pro-nucleotide into the respective nucleosid-5'-yl phosphate.

The aims defined and the solutions to the problems associated with their realization, are achieved in this invention.

DETAILED DESCRIPTION

The subject matter of the invention is a nucleotide analogue of the formula (XVII)

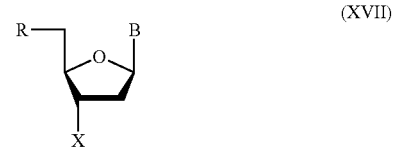

(XVII)

where R stands for a phosphoramidate residue based on aminopyridine derivatives of the formula (XVIII)

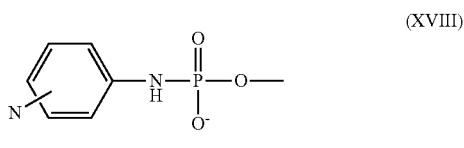

characterized in that that it is described by the formula (XIII)

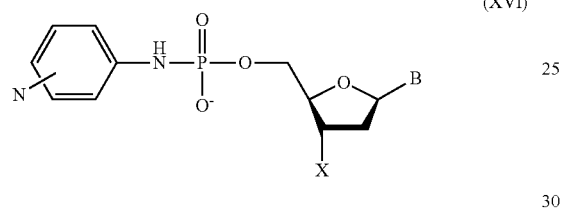

described preferably by the formula (XVI)

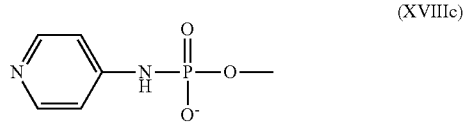

where X stands for $N_3$ and B stands for thymidine-1-yl, or X stands for H and B stands for uracil-1-yl or adenin-1-yl or hypoxantin-1-yl.

Preferably, the phosphoramidate residue is based on aminopyridine derivatives, preferably 4-aminopyridine, and preferable it is a phosphoramidate monoester described by the formula (XVIIIc)

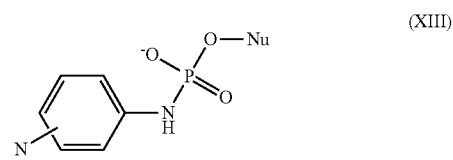

preferably in the form of phosphate derivative with proton as an counter ion or other pharmacologically accepted salt, preferably potassium or sodium salts.

Preferably, the analogue is an anti-HIV pro-nucleotide.

Preferably, endocyclic nitrogen atom in the formula (XVIII) is placed in 2-, 3- or preferably 4-position.

Preferably, the nucleotide analogue does not have chiral centers at the phosphorus atom.

Preferably, the nitrogen base in the formulas (XVI) and (XVII) is thymine, uracil, adenine or hypoxanthine, preferably thymine if $X=N_3$.

The next subject of the invention is the way of synthesis and preparation of the nucleotide analogues characterized in that the synthesis of nucleoside phosphor[N-(pyridin-Zyl)]amidates in which Z indicates the position of the nitrogen atom in the pyridine ring and it is a number 2 or 3, the nucleoside analogues depicted with formula (XIII)

which synthesis is carried out according to the scheme below

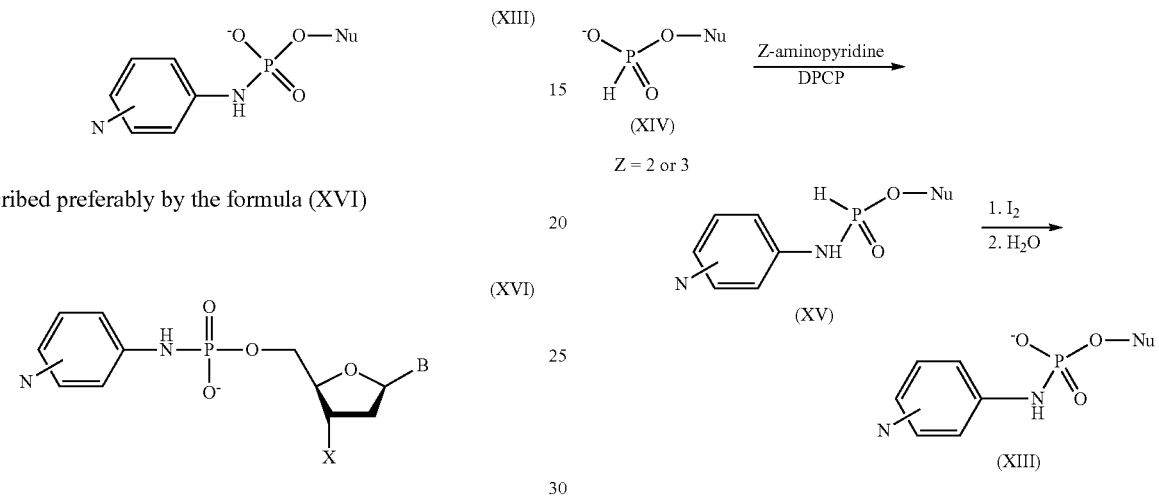

and where the compound (XIII) is describe by means of formula (XVI)

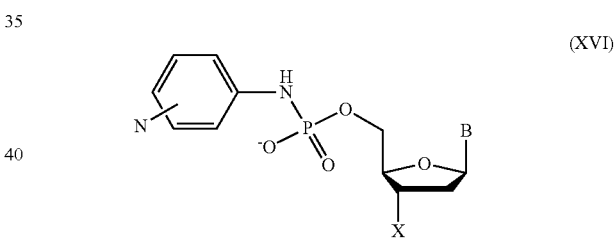

in which X and B are identical as in the compounds depicted with formulas (XVITa,b), (XVIUa,b) (XVIAa,b) and (XVI-Ha,b) presented below

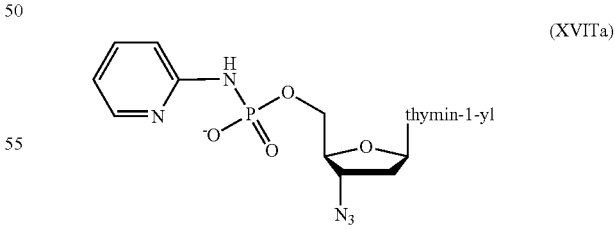

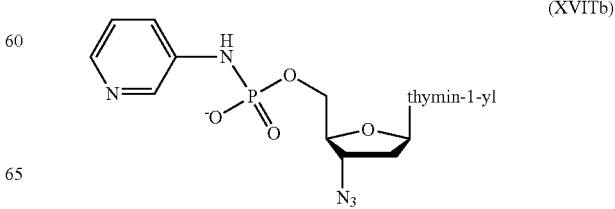

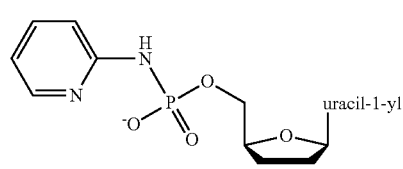

(XVIUa)

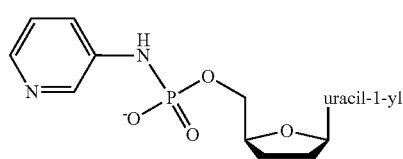

(XVIUb)

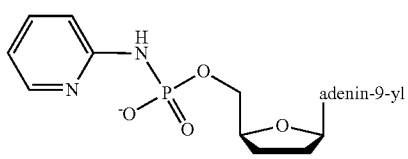

(XVIAa)

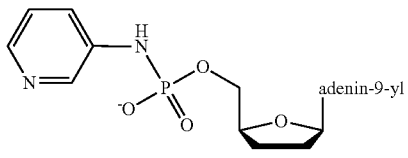

(XVIAb)

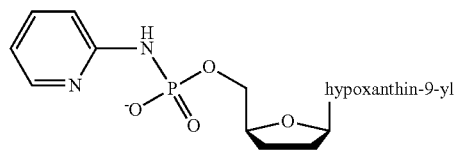

(XVIHa)

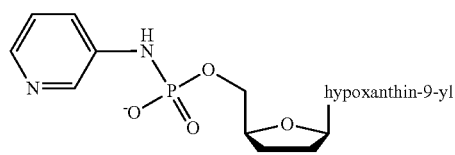

(XVIHb)

Preferably when nucleoside analougues are AZT, ddU, ddA and ddI.

Preferably when 1 molar equivalent of nucleosid-5′-yl H-phosphonate described with formula (XIV) and 3 molar equivalents of 3-aminopyridine were dissolved in pyridine, which was subsequently evaporated under reduced pressure and to the remaining residue dissolved in the mixture of methylene chloride and pyridine 1:1 (v/v) so that the concentration of 10 mL/1 mmol of compound (XIV) is achieved, at least 1 molar equivalent of diphenyl chlorophosphate (DPCP) is added. After 15 min the formation of phosphonoamidate (XV) is completed, and to the reaction mixture at least 1 molar equivalent of iodine in pyridine (in concentration 1 mmol/1 mL) containing at least 10 molar equivalents of water was added, and after 5 min the excess of iodine is decomposed with added ethanethiol until the solution is discoloured and after evaporation of the solvent under reduced pressure and dissolving the remaining oily residue in water to concentration of 10 mL/1 mmol as calculated for the substrate (XIV), the whole is washed with methylene chloride (two portions of equal volumes) and after separation, the water layer is evaporated and the residue, dissolved in toluene/methanol 7:3 (v/v) is applied to the column loaded with silica gel and the product is isolated using isocratic conditions with toluene/methanol 7:3 (v/v) as solvent system, and the fractions containing pure product (XVI) are collected, and evaporated and the remains are lyophilized from frozen mixture of methanol and benzene, yielding pure product as a white dry powder with the yield exceeding 60%.

Preferably when for the synthesis of nucleosid-5′-yl phosphor[N-(pyridin-4-yl)]amidates described with formula (XVIc), the phosphorylating agent described with formula (XIX) is used and for phosphorylation of nucleoside analogues described with formula (XXT) nucleoside is AZT, described with formula (XXIU) nucleoside is ddU, described with formula (XXIA) nucleoside is ddA, and described with formula (XXIH) nucleoside is ddI, di(1H-1,2,4-triazol-1-yl)phosphor[N-(pyridin-4-yl)amidate described with formula (XIX) is used and the reaction is carried out according to scheme

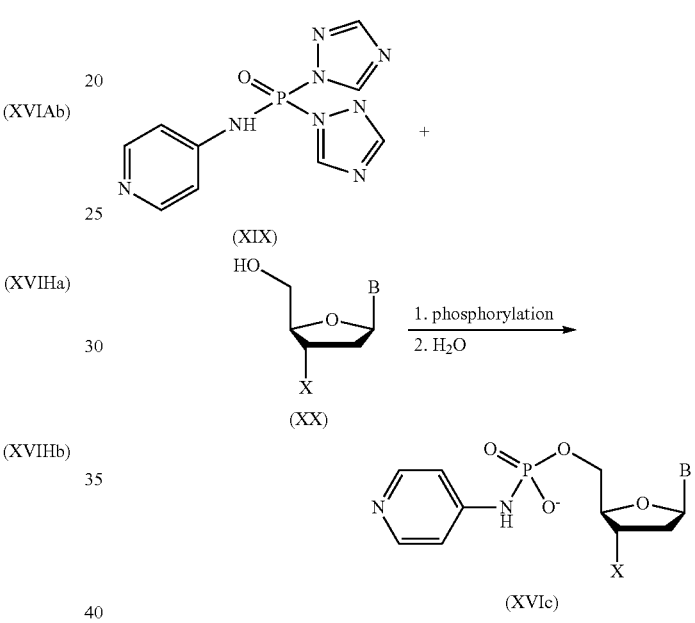

and the obtained final nucleotide derivatives are described with formula (XVIc), where for (XXT) and (XVITc): X=N₃, B=thymine; for (XXU) and (XVIUc): X=H, B=uracil; for (XXA) and (XVIAc): X=H, B=adenine; and for (XXH) and (XVIHc): X=H, B=hypoxanthine.

Preferably when to a stirred suspension of 2 molar equivalents of di(1H-1,2,4-triazole)phosphor[N-(pyridin-4-yl)]amidate (XIX) in pyridine in concentration of 1 mmol/12.5 mL and heated up to 75° C. (oil bath), at least 1 molar equivalent of nucleoside described with formula (XX) dissolved in pyridine (concentration 1 mmol/10 mL) is added and the reaction is continued for at least 4 min at 75° C., and cooled down to room temp. Then a large excess of water is added, the whole is left for 1 h, solvent is evaporated andthe remains dissolved in water (10 mL/1 mmol of nucleoside) is washed with methylene chloride (3 times, 25 mL/1 mmol of nucleoside) and the water layer is evaporated and the crude product dissolved in minimum volume of methanol/toluene 1:1 (v/v), is subjected for purification on the column loaded with silica gel. The isolation is carried out using isocratic conditions with methanol/toluene 1:1 (v/v) as solvent system, and the fractions containing pure compound of type (XVIc) are collected and evaporated yielding pure product described with formula (XVIc)

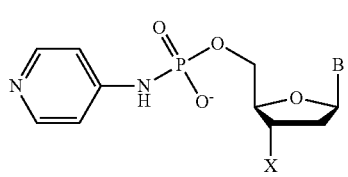
(XVIc)

obtained as white dry powder with the yields exceeding 50%.

Preferably when compound described with formula (XVIc) is obtained

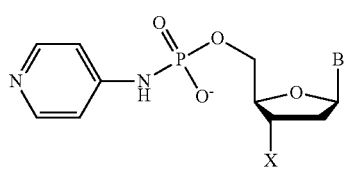
(XVIc)

and preferably compounds described with below formulas

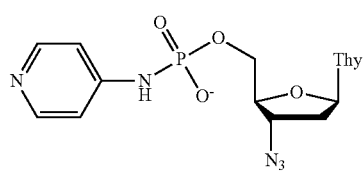
(XVITc)

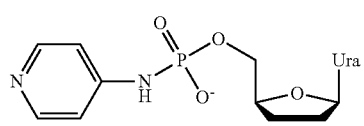
(XVIUc)

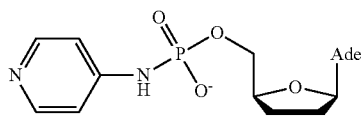
(XVIAc)

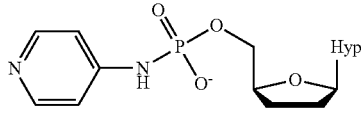
(XVIHc)

The next subject matter of invention is application of nucleotide described above as antiviral pro-nucleotide, preferably derivative of 4-aminopyridine, preferably against HIV.

Preferably, the nucleotide analogue is used for preparation of an antiviral drug, preferable a drug for AIDS treatment.

The next subject of the invention is antiviral pro-nucleotide, the nucleotide analogue described above.

The next subject of the invention is a pharmaceutical composition comprising the nucleotide analogue described above.

Preferably, when pharmaceutical composition is an antiviral drug, preferentially for treatment of HIV infections including AIDS.

The next subject of the invention is phosphorylating agent for preparation of nucleotide analogue described above, and characteristic with that that is described with formula (XIX)

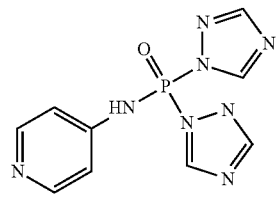
(XIX)

and that it introduces into nucleosides phosphor[N-(pyridin-4-yl)amidate residue.

Preferably, when phosphorylating agent described above is used for phosphorylation of nucleosides described with formula (XX)

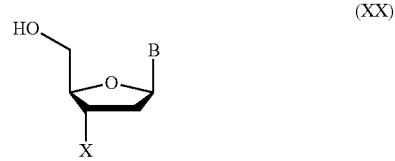
(XX)

and particularly where formula (XXT) is AZT, formula (XXU) is ddU, formula (XXA) is ddA and formula (XXH) is ddI.

EXAMPLES

Synthesis of nucleosid-5'-yl phosphor[N-(pyridin-Z-yl)]amidates of Type XVIa and XVIb In the synthesis of nucleosid-5'-yl phosphor[N-(pyridin-Z-yl)]amidates (in which Z indicates the position of nitrogen atom in the pyridine ring and corresponds to numbers 2 or 3) which are the subject matter of the invention, there were applied results of studies in which it was found that phosphon (N-aryl)amidates, opposite to their N-alkyl congeners, easily underwent oxidation with iodine towards respective phosphor(N-aryl)amidates including phosphor[N-(pyridin-Z-yl)]amidates. This discovery was used in elaboration of the new method for synthesis of phosphor[N-(pyridin-Z-yl)]amidates (in which Z indicates the position of the nitrogen atom in pyridine ring and corresponds to numbers 2 or 3) of nucleoside analogues as AZT, ddU, ddA and ddI as a new compounds active against HIV.

Synthesis phosphor[N-(pyridin-Z-yl)]amidates (in which Z indicates the position of the nitrogen atom in the pyridine ring and corresponds to numbers 2 or 3) of nucleoside analogues depicted with formula (XIII),

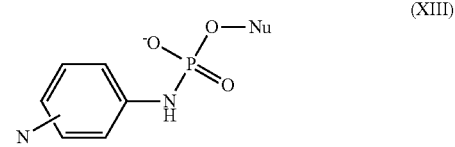
(XIII)

was performed as shown in Scheme 1 and followed the procedure described below.

Scheme 1
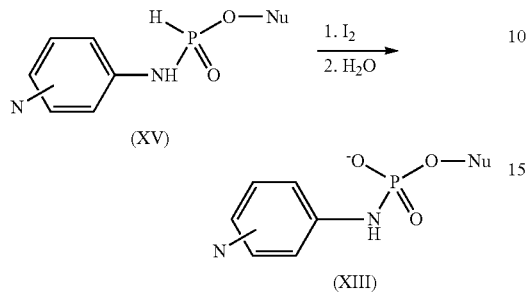
And more precisely compound (XIII) can be depicted with formula (XVI)
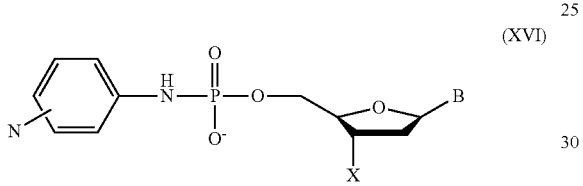
in which X and B are identical as in compounds (XVITa,b), (XVIUa,b), (XVIAa,b) and (XVIHa,b) presented below.
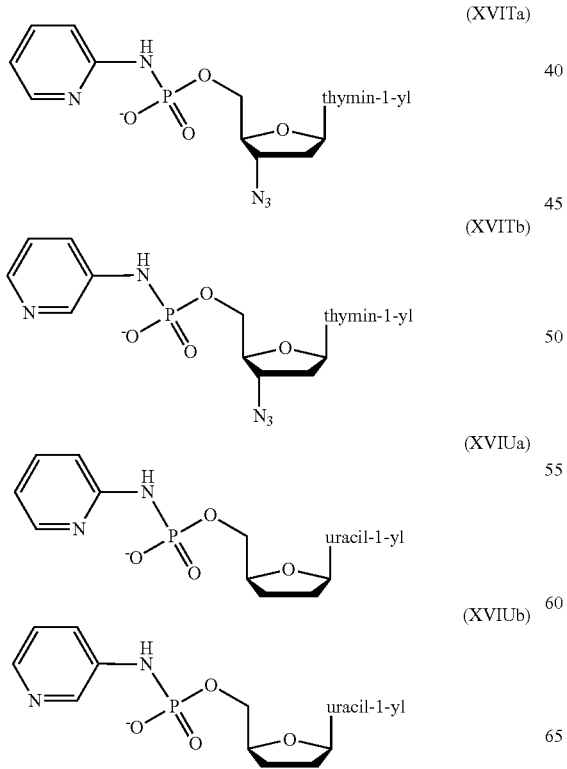
Example 1
Synthesis of nucleosid-5'-yl phosphor [N-(pyridin-3-yl)]amidate—derivative of 3'-azido-3'-deoxythymidine (AZT) Described with Formula (XVITb)
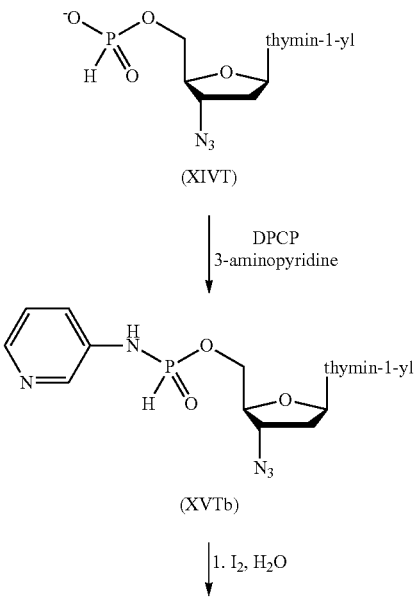

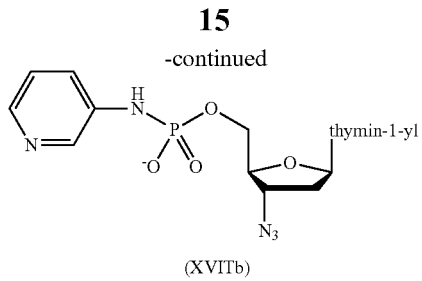

(XVITb)

To remove traces of water, from nucleosid-5'-yl H-phosphonate (XIVT) (Scheme 2) (1 molar equiv.) and 3-aminopyridine (3 molar equiv.) dissolved in pyridine, solvent was evaporated under reduced pressure (rotary evaporator). To the remaining residue dissolved in the mixture of methylene chloride and pyridine 1:1 (v/v) (10 mL/1 mmol) diphenyl chlorophosphate (DPCP) was added (1.1 molar equiv.). After 15 min the formation of phosphonamidate (XVTb) was completed, what was found with $^{31}$P NMR spectra of reaction mixture, which showed disappearance of the signal derived from substrate (XIVT) (~3 ppm) and the presence of two signals in the region~5-6 ppm generated by two diastereoisomers of H-phosphonamidate (XVTb). To this iodine (2 molar equiv.) in pyridine (1 mmol/mL) containing water (50 molar equiv.) was added. After 5 min the excess of iodine was decomposed with ethanthiol (to discolour the solution). Then solvent was removed under reduced pressure (rotary evaporator), the remaining oily residue was dissolved in water [10 mL/1 mmol as calculated for the substrate (XIVT)], and this was washed with methylene chloride (two portion of equal volume). After separation, the water layer was evaporated (rotary evaporator) and residue was dissolved in a mixture toluene/methanol 7:3 (v/v) and applied to the column loaded with silica gel 60 (4×6 cm for separation in 1 mmol scale). The product was isolated using isocratic conditions with a mixture toluene/methanol 7:3 (v/v). Fractions containing pure product (XVITb) were collected and evaporated. The remaining oily residue was dissolved in a mixture of methanol and benzene, frozen and lyophilized. Product (XVITb, vide infra), derivative of AZT, was obtained as a white dry powder. Yield 91%.

(XVITb)

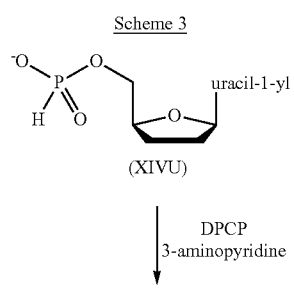

Example 2

Synthesis of nucleosid-5'-yl phosphor[N-(pyridin-3-yl)]amidate—a Derivative of 2',3'-dideoxyuridine Described with Formula (XVIUb)

Scheme 3

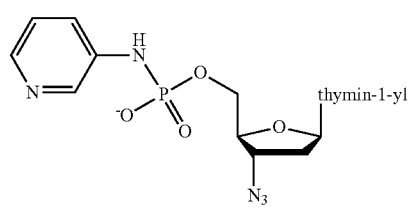

(XIVU)

↓ DPCP
3-aminopyridine

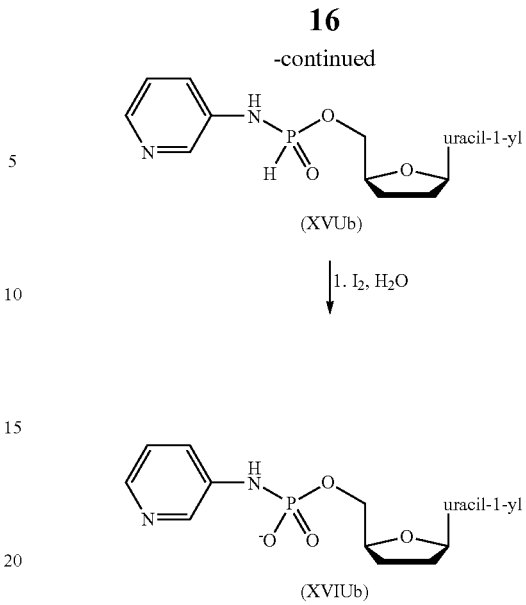

(XVUb)

↓ 1. I$_2$, H$_2$O (XVIUb)

The synthesis of compound (XVIUb) was carried out as described in Example 1. It was obtained derivative of ddU presented with formula (XVIUb) with 88% yield.

(XVIUb)

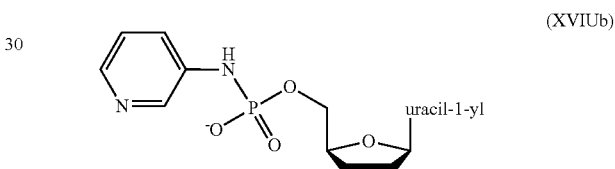

Example 3

Synthesis of nucleosid-5'-yl phosphor[N-(pyridin-3-yl)]amidate—a Derivative of 2',3'-dideoxyadenosine Described with Formula (XVIAb)

Scheme 4

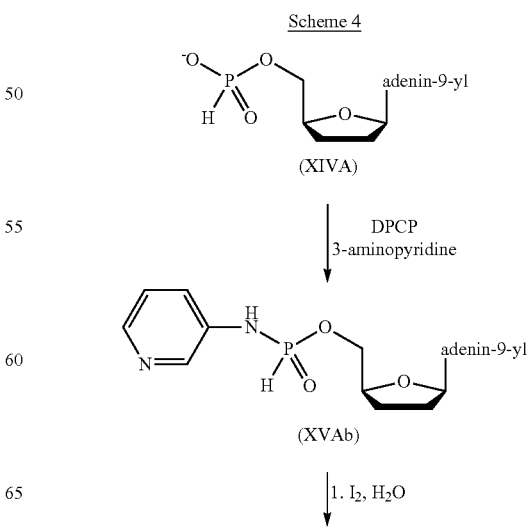

(XIVA)

↓ DPCP
3-aminopyridine (XVAb)

↓ 1. I$_2$, H$_2$O

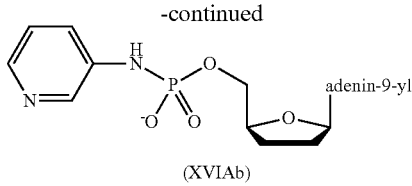

(XVIAb)

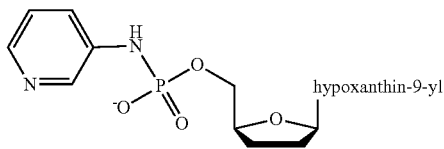

(XVIHb)

The synthesis of compound (XVIAb) was carried out as described in Example 1. It was obtained derivative of ddA presented with formula (XVIAb). Yield 77%.

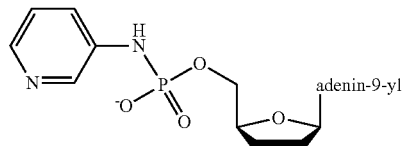

(XVIAb)

Example 4

Synthesis of nucleosid-5'-yl phosphor[N-(pyridin-3-yl)]amidate—a Derivative of 2',3'-dideoxyinosine Described with Formula (XVIHb)

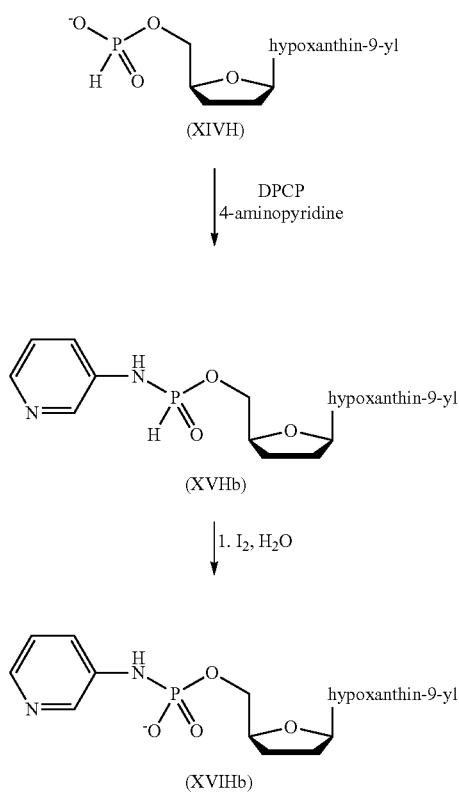

The synthesis of compound (XVIHb) was carried out as described in Example 1. It was obtained derivative of ddI presented with formula (XVIHb) Yield 80%.

Obtained Yields:
(XVITa)-90%; (XVITb)-91%; (XVIUa)-92%; (XVIUb)-88%; (XVIAa)-82%; (XVIAb)-77%; (XVIHa)-73%; (XVIHb)-80%.

Examples Cont.

Synthesis of nucleosid-5'-yl phosphor[N-(pyridin-4-yl)amidates of Type (XCIc)

Because of the method described above in the case of nucleosid-5'-yl phosphor[N-(pyridin-4-yl)amidates of type (XVIc) was unsuccessful, a new method based on the new original phosphorylating agent was found, which made possible the introduction of phosphor[N-(pyridin-4-yl)amidate moiety into nucleosides. A new phosphorylating agent di(1H-1,2,4-trazole) phosphor[N-(pyridin-4-yl)]amidate (XIX) was obtained from phosphoryl-tris-(1H-1,2,4-triazole) [A. Kraszewski et al,. *Tetrahedron Lett.,* 1980, 21, 2935-2936] according to procedure described by us [A. Kraszewski et al.,] in *J. Med Chem.,* 2011, 54, 6482-6491

With the use of di(1H-1,2,4-triazole) phosphor[N-(pyridin-4-yl)]amidate (XIX) for phosphorylation of nucleoside analogues of type (XX) [(XXT)—AZT; (XXU)—ddU; (XXA)—ddA; (XXH)—ddI)] in reactions sequence depicted in Scheme 6, the final nucleotides of type (XVIc) were obtained (Scheme 6).

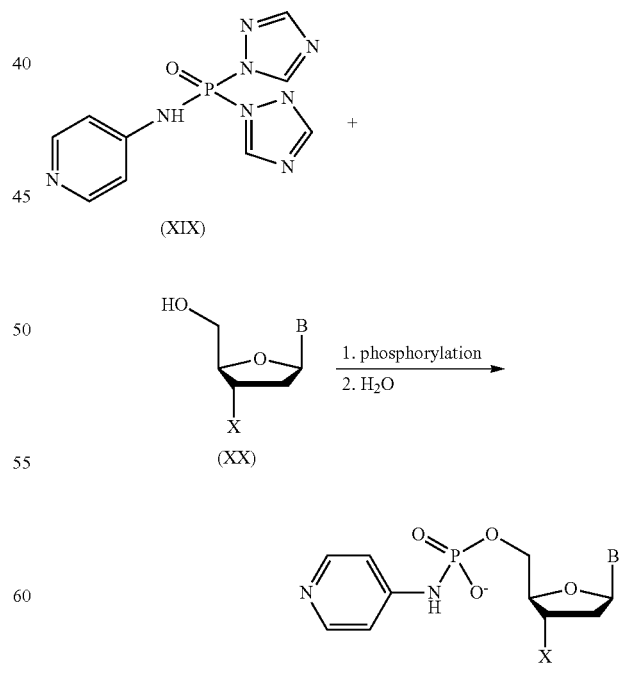

(XXT) and (XVITc) - X = N3, B = thymine; (XXU) and (XVIUc) - X = H, B = uracil; (XXA) and (XVIAc) - X = H, B = adenine; (XXH) and (XVIHc) - X = H, B = hypoxantine

Example 5

Synthesis of 3'-azido-3'-deoxythymidin-5'-yl phosphor[N-(pyridin-4-yl]amidate (XVITc)

Scheme 7

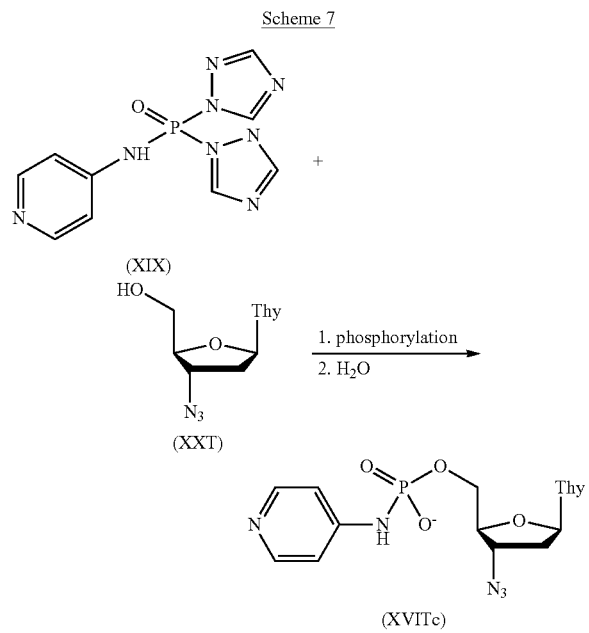

To a suspension of di(1H-1,2,4-triazole)phosphor[N-(pyridin-4-yl]amidate (XIX) (2 molar equiv.) (Scheme 7) in pyridine (1 mmol/12.5 mL) heated up to 75° C., AZT (XXT) (1 molar equiv.) dissolved in pyridine (1 mmol/10 mL) was added in five equal portions with vigorous stirring and the reaction was continued for 5 min at 75° C., cooled down to room temp., quenched with water (ca 50 molar equiv.) and left for 1 h. The solvent was evaporated (rotary evaporator) and the remaining oily residue was dissolved in water (10 mL/1 mmol of nucleoside) was washed with methylene chloride (3×25 mL/1 mmol of nucleoside). The aqueous layer was evaporated to an oil and crude product, dissolved in a minimum volume of methanol/toluene 1:1 (v/v), was subjected to purification on the column loaded with silica gel. The isolation was carried out by using isocratic conditions and methanol/toluene 1:1 (v/v) as solvent system. Fractions containing pure compound (XVITc) were collected and evaporated. After lyophilization from frozen solution (mixture of benzene and methanol) pure product (XVITc) was obtained as white dry powder.

The compound depicted with formula (XVITc) was obtained in 62% yield.

(XVITc)

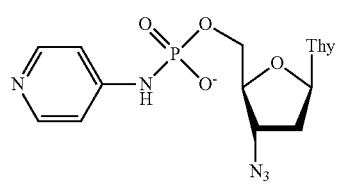

Example 6

Scheme 8

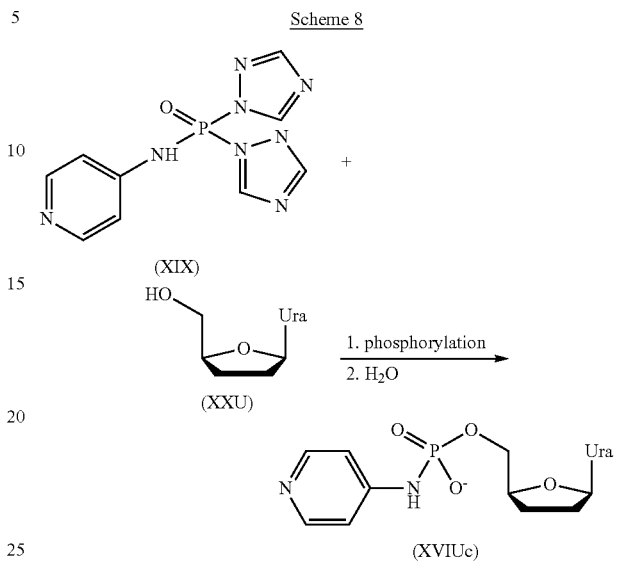

The synthesis of compound (XVIUc) (Scheme 8) was carried out as described in Example 5. It was obtained derivative of ddU which is presented with formula (XVIUc). Yield 58%.

(XVIUc)

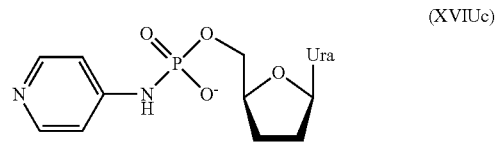

Example 7

Scheme 9

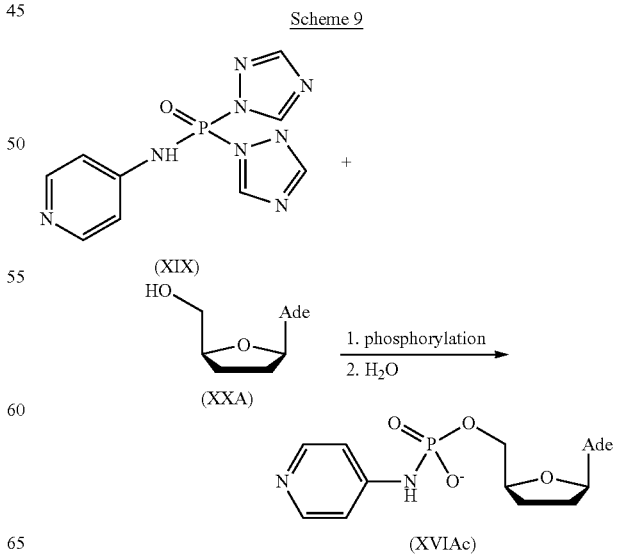

The synthesis of compound (XVIAc) (Scheme 9) was carried out as described in Example 5. It was obtained derivative of ddA which is presented with formula (XVIAc). Yield 58%.

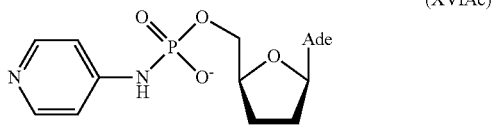

(XVIAc)

Example 8

Scheme 10

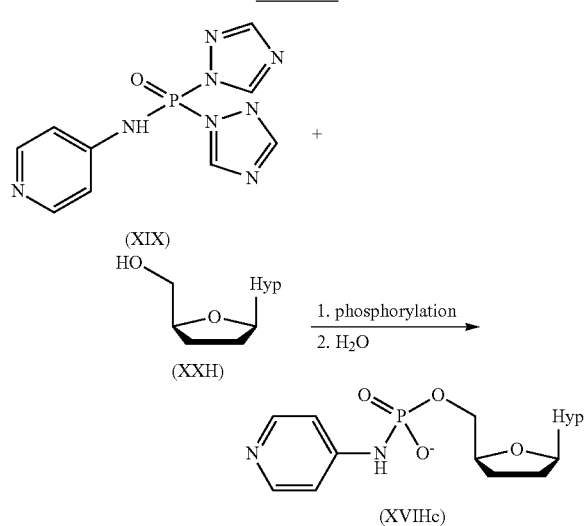

The synthesis of compound (XVIHc) (Scheme 10) was carried out as described in Example 5. It was obtained derivative of ddI which is presented with formula (XVIHc). Yield 58%

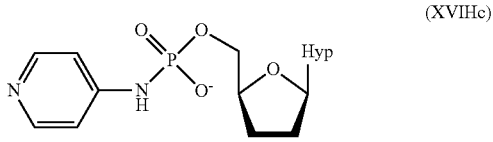

(XVIHc)

Cytotoxicity and Activity anti-HIV Compounds (XVIa-c)

Cytotoxicity and anti-HIV activity of the compounds (XVIa-c) described above were examined in CEM-T4 cells according procedures described below.

Cytotoxicity determination—$CC_{50}$ and $CC_{90}$ parameters—For determination of compounds (XVIa-c) cytotoxicity CEM-T4 and CEM-A were cultured in standard conditions (37° C., 5% $CO_2$) on 96 wells culture plates in media RPMI/FCS 10% (v/v). Experiments were carried out in media contained tested compounds in concentrations of appropriate range. Cultures in neat medium (RPMI, 10% FCS) were used as a control ones. Viability of cells were determined after 7 days using MTT test in which to each well of culture plate were added 10 μL of MTT solution (5 mg/mL) and cultures were incubated 3 hours in temperature 37° C. After centrifugation supernatant was removed and DMSO was added to lyse the cells and to dissolve crystals of farmazan. Measurement of colour intensity was done using a plate reader ($\lambda_{560\,nm}$).

Cytotoxicity calculation—reference absorbancy (K) was an average of measurements for five well of culture plate and accounts for 100% CEM-T4 or CEM-A cells viability. In each case absorbancy for cells cultured in media enriched with tested compounds was calculated as average of at least three measurements.

Cells viability (P) were calculated according to formula:

$$P = \frac{(A - T) \times 100}{K - T}[\%]$$

in which P—viability of cells, K—reference absorbancy, A—absorbancy for cells cultured in media enriched with tested compounds, T—absorbancy for neat medium (RPMI/10% FBS). On the basis of calculations graph showing dependence of viability and concentrations of tested compounds values of $CC_{50}$ and $CC_{90}$ were determined Anti HIV activity ($EC_{50}$ and $EC_{90}$)—parameter $EC_{50}$ is defined as concentration of compounds in which replication of HIV is inhibited by 50% and parameter $EC_{90}$ is defined as concentration of compounds in which replication of HIV is inhibited by 90%. To determine these parameters CEM-T4 cells were preincubated 24 hours in standard conditions (37° C., 5% $CO_2$) in standard medium [RPMI, FCS 10% (v/v)] enriched with tested compounds in concentrations in range 0.001-20 μM. Incubations were performed with 96 flat bottom wells culture plates. In each well 20000 cells were suspended in solution of tested compound (200 μL). For each concentration four cultures were done. As a reference, media containing AZT in concentration 1.25 μM, 2.5 μM, 5.0 μM, 10.0 μM, 20 μM were used. As a positive control of maximal replication of HIV, culture in neat standard medium [RPMI/FCS 10% (v/v)] was used. After 24 hours of incubation in medium enriched with tested compound and AZT, cells were inoculated with known amount of HIV and cultivation was continued 8 days and after this the amount of viral protein p24 (marker of HIV replication) was measured. Inhibition of HIV replication is presented as percentage of p24 content in culture performed with media containing tested compound and assuming that amount of p24 measured in control correspond 100% of HIV replication. The examinations of each tested substance for each concentration were run in triplicate.

TABLE 1

Cytotoxicity (CC) and anti-HIV activity (EC) of selected series of compounds (XVIc) and nucleosides (XX) they derived from.

| Compound | $CC_{50}$ [μM] | $CC_{90}$ [μM] | $EC_{50}$ [μM] | $EC_{90}$ [μM] | $SI_{50}$ |
|---|---|---|---|---|---|
| (XVITc) | >>190 | >>190 | 0.0011 | 0.006 | >>19000 |
| AZT | 60 | — | 0.0011 | 0.016 | 6000 |
| (XVIUc) | >>1000 | >>1000 | 0.44 | >1 | >>2273 |
| ddU | >>250* | — | 48* | — | >>5.2* |
| (XVIAc) | >>1000 | >>1000 | 1.7 | 2.65 | >>588 |
| ddA | >>250* | — | 2.5* | — | >>100* |
| (XVIHc) | >>5300 | >>5300 | 20.00 | >20 | >>215 |
| ddI | >>100** | — | 1.1** | — | >>91** |

*Estimated in cells CEM-T4; Baba M. et al., *Biochem. Biophys. Res. Commun.*, 1987, 142(1), 128-134;
**Imbach J-L., et al., *Biochem. Pharmacol.*, 1994, 48(1), 11-14

Compounds obtained by Applicants constitute a new group of nucleotide derivatives, which cytotoxicity were lower (or much lower) than nucleosides they derived (AZT and ddU) and which anti-HIV potencies were comparable or markedly better than parent nucleosides. They are pro-nucleotides what was proved by observed anti-HIV activity of ddU derivative. This feature and very good solubility in water, as well as very low cytotoxocity and retained anti-HIV activity make Applicants compounds more valuable as a potential therapeutics against HIV as compare to drugs applied in AIDS therapy so far.

The following basic properties of examined compounds make them a potential therapeutics:
very good solubility in aqueous media [phosphoric buffer pH 7.5, cell culture medium (RPMI/FBS 9:1 (v/v)],
comparable or higher anti-HIV activity than the parent nucleosides,
low cytotoxicity,
the compounds are pro-nucleotides,
the compounds are stable during storage,
the compounds do not contain chiral centres, which may affect their biological activity,
because the compounds are stable (7 days) in aqueous buffers of pH=1, i. e. the acidity identical as in the stomach, they are promising candidates for oral delivery.

We claim:

1. A nucleotide analogue described by formula (XVII)

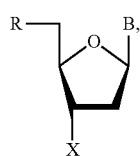

(XVII)

where R is a phosphoramidate derivative of aminopyridines, described by formula (XVIII)

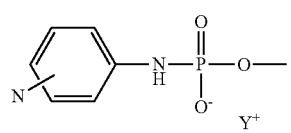

(XVIII)

and therefore having the structural formula (XIII),

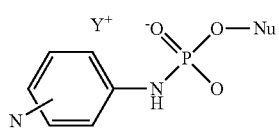

(XIII)

and alternatively described with formula (XVI)

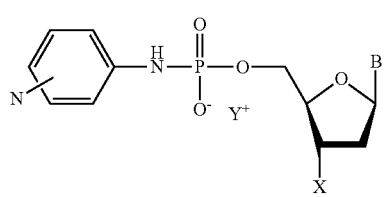

(XVI)

where X is $N_3$ and B is thymin-1-yl, or X is H and B is uracil-1-yl, adenin-9-yl or hypoxanthin-9-yl, and $Y^+$ is inorganic or organic cation.

2. The nucleotide according to claim 1, wherein nitrogen atom N in the formula (XVIII) is placed in position 2-, 3- or 4-.

3. The nucleotide analogue according to claim 1, wherein a phosphoramidate fragment derives from 4-aminopyridine phosphoramidate is described with the formula (XVIIIc) shown below:

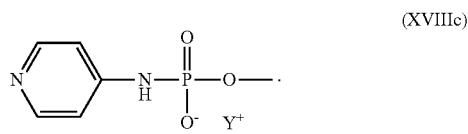

(XVIIIc)

4. The nucleotide analogue according to claim 3, wherein the cation associated with the phosphoramidate moiety is selected from H, sodium ion and potassium ion.

5. The nucleotide analogue according to claim 3, wherein the aminopyridine portion of structure (XVIII) is associated with the phosphoramidate moiety selected from 2-pyridinylamino, 3-pyridinylamino, and 4-pyridinylamino.

6. A pharmaceutical composition comprising a compound of claim 1 in combination with a pharmaceutically acceptable carrier or excipient.

7. The nucleotide analogue according to claim 1, wherein nitrogen atom N in the formula (XVIII) is placed in position 4-.

8. The nucleotide analogue according to claim 1, wherein the nucleobase B in the formulas (XVI) and (XVII) is thymin-1-yl, uracil-1-yl, adenin-9-yl, or hypoxanthin-9-yl.

9. The nucleotide analogue according to claim 1, wherein the nucleobase B in the formulas (XVI) and (XVII) is thymin-1-yl when $X=N_3$.

10. A method of synthesis of the nucleotide analogues according to claim 1, comprising: synthesis of phosphor[N-(pyridin-Z-yl)]amidates of nucleoside analogues described by formula (XIII), where Z indicates the position of the nitrogen atom in the pyridine ring and it is a number 2, 3 or 4

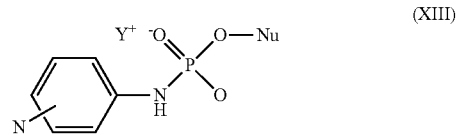

(XIII)

carried out according to the scheme below (XIV) Z = 2 or 3

(XV)

(XIII)

where DPCP is diphenyl chlorophosphate and the compound (XIII) is alternatively defined by described with formula (XVI)

(XVI)

in which Y+ is inorganic or organic cation, and X and B are the same as in the compounds depicted with formulas (XVITa,b), (XVIUa,b), (XVIAa,b) and (XVIHa,b) presented below, (XVITa) thymin-1-yl (XVITb) thymin-1-yl (XVIUa) uracil-1-yl (XVIUb) uracil-1-yl (XVIAa) adenin-9-yl (XVIAb) adenin-9-yl (XVIHa) hypoxanthin-9-yl (XVIHb) hypoxanthin-9-yl.

11. The method according to claim 10, wherein the nucleoside analogue is AZT, ddU, ddA, or ddI.

12. The method according to claim 10, further comprising:
dissolving a mixture of 1 mol equivalent of XIV and 3 mol equivalent of 3-aminopyridine in pyridine and evaporating the solvent under reduced pressure;
redissolving the residue in methylene chloride/pyridine 1:1 (v/v) to achieve a concentration of 10 ml/1 mmol;
adding at least 1 mol equivalent of diphenyl chlorophosphate (DPCP);
after 15 min when the formation of phosphonoamidate (XV) was completed, treating the mixture with a solution of at least 1 mol equivalent of iodine in pyridine (1 ml/1 mmol) containing at least 10 equivalent of water;
after 5 min, decomposing an excess of iodine by adding ethanethiol to disappear color;
evaporating the solvents under reduced pressure;
dissolving the oily residue in water (10 ml/1 mmol of XIV) and washing the solution twice with the same volume of methylene chloride;
separating and evaporating the water phase;
dissolving the residue in toluene/methanol 7:3 (v/v) and applying the dissolved residue onto a column loaded with silica gel
isolating the product under isocratic conditions with toluene/methanol 7:3 (v/v) as a solvent system;
collecting and evaporating the fractions containing pure product (XVI); and
lyophilizing the remains from a frozen mixture of methanol and benzene, yielding a pure product as a white dry powder in the yield of more than 60%.

13. The method according to claim 10, wherein di(1H-1,2,4-triazol-1-yl)phosphor[N-(pyridin-4-yl)amidate described with formula (XIX) is provided as the phosphorylating agent in the synthesis of nucleosid-5'-yl phosphor[N-(pyridin-4-yl)]amidates described with formula (XVIc), and in the phosphorylation of nucleoside analogues described with formula (XX)=(XXT), (XXU), (XXA) or (XXH) in which (XXT) is AZT, (XXU) is ddU, (XXA) is ddA, and (XXH) is ddI, di(1H-1,2,4-triazol-1-yl)phosphor[N-(pyridin-4-yl)amidate described with formula (XIX) is provided and the synthesis is carried out as presented in the following scheme

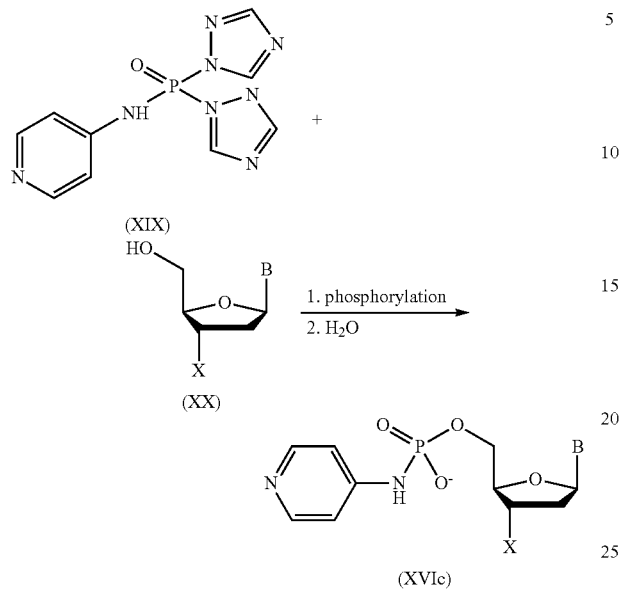

and the obtained final nucleotide derivatives are described with formula (XVIc), where for (XXT) and (XVITc): X=N₃, B=thymin-1-yl; for (XXU) and (XVIUc): X=H, B=uracil-1-yl; for (XXA) and (XVIAc): X=H, B=adenin-9-yl; and for (XXH) and (XVIHc): X=H, B=hypoxanthin-9-yl, and Y⁺is inorganic or organic cation.

14. A method according to claim 10, further comprising:
adding a solution of at least 1 mol equivalent of compound XX in pyridine (10 ml/1 mmol) portionwise to a vigorously stirred suspension of 2 mol equiv. of di(1H-1,2,4-triazole)phosphor[N-(pyridin-4-yl)amidate (XIX) in pyridine (12.5 ml/1 mmol) at 75 °C.; heating the mixture for at least 4 h, cooled down to room temperature;
adding a large excess of water and letting the mixture set for 1 h;
evaporating solvent;
re-dissolving the residue in water (10 ml/1 mmol of nucleoside) and washing the re-dissolved residue with methylene chloride (3×25 ml/1 mmol of nucleoside); and
evaporating the water phase; dissolving the residue in a minimal amount of methanol/toluene 1:1 (v/v) and subjecting the dissolved residue to purification on the column loaded with silica gel, wherein the isolating is carried out using isocratic conditions with methanol/toluene 1:1 (v/v) as a solvent system, and the fractions containing pure compound of type (XVIc) are collected and evaporated and after

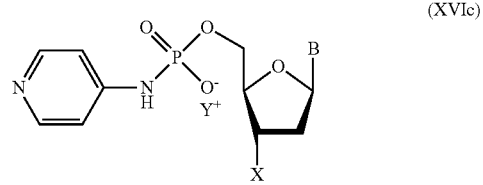

(XVIc)

lyophilization from frozen benzene/methanol, the pure product described with formula (XVIc) is obtained as white dry powder in the yield of more than 50%.

15. The method according to claim 14, further comprising specific compounds of the generic formula (XVIc) are obtained,

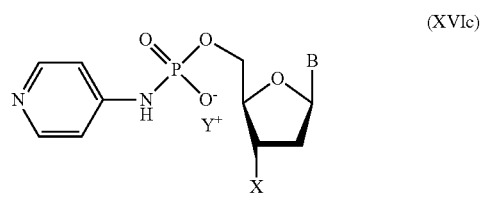

(XVIc)

and specific compounds are individually defined by the following formulas

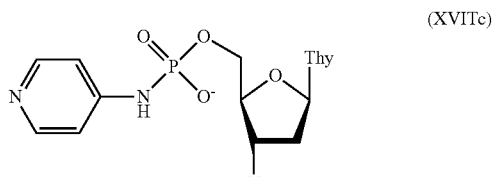

(XVITc)

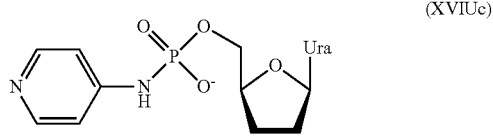

(XVIUc)

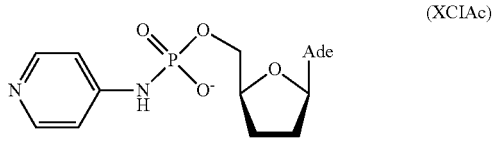

(XCIAc)

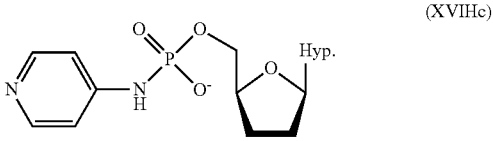

(XVIHc)

16. A method of treating HIV in a host in need thereof by the administration of an effective dosage of a compound of claim 1 to the host.

17. The method of making a pharmaceutical composition comprising a compound of claim 1 by the admixture of a compound of claim 1 with one or more pharmaceutically acceptable carriers or excipients.

* * * * *